United States Patent [19]

Sih

[11] 4,267,371
[45] May 12, 1981

[54] 19-HYDROXY-6A-CARBA-PGI$_2$ AMIDES

[75] Inventor: John C. Sih, Portage, Mich.

[73] Assignee: The Upjohn Company, Kalamazoo, Mich.

[21] Appl. No.: 126,468

[22] Filed: Mar. 3, 1980

Related U.S. Application Data

[62] Division of Ser. No. 54,811, Jul. 5, 1979, Pat. No. 4,225,508.

[51] Int. Cl.$^3$ .......................................... C07C 103/19
[52] U.S. Cl. .................................................... 564/188
[58] Field of Search ...................... 260/557 B; 560/121

[56] References Cited

U.S. PATENT DOCUMENTS

| Re. 30,287 | 5/1980 | Marx et al. | 560/121 X |
| 4,169,895 | 10/1979 | Hess et al. | 260/556 AC X |
| 4,191,694 | 3/1980 | Skuballa et al. | 260/556 AC X |

FOREIGN PATENT DOCUMENTS

| 2505519 | 8/1975 | Fed. Rep. of Germany | 560/121 |
| 2012265 | 7/1979 | United Kingdom . | |
| 2013661 | 8/1979 | United Kingdom . | |

Primary Examiner—Thomas A. Waltz
Attorney, Agent, or Firm—Robert A. Armitage

[57] ABSTRACT

The present invention provides novel 19-hydroxy-6a-carba-PGI$_1$ amides which are useful for pharmacological purposes, e.g., anti-asthmatic indications.

1 Claim, No Drawings

19-HYDROXY-6A-CARBA-PGI₂ AMIDES

DESCRIPTION

CROSS REFERENCE TO RELATED APPLICATION

The present invention is a divisional application of U.S. Ser. No. 054,811, filed July 5, 1979, now U.S. Pat. No. 4,225,508.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-6a-carba-PGI₂ amides. The novel prostacyclin analogs are useful for pharmacological purposes, e.g., as anti-asthmatic agents. The preparation and use of these compounds is incorporated here by reference from U.S. Ser. No. 054,811, filed July 5, 1979.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI₂, see R. A. Johnson, et al., Prostaglandins 15, 737–740 (1978).

SUMMARY OF THE INVENTION

The present invention particularly provides a prostacyclin-type compound of the formula

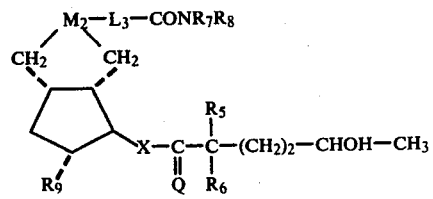

wherein $L_3$ is
(1) —$(CH_2)_n$—, wherein n is one to 5, inclusive,
(2) —$(CH_2)_p$—$CF_2$—, wherein p is 2, 3, or 4, or
(3) —$CH_2$—$CH$=$CH$—;
wherein $M_2$ is

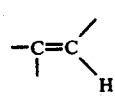 (1)

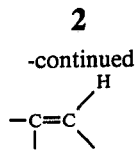 (2)

wherein Q is oxo, α-H:β-H, α-OH:β-$R_4$, or α-$R_4$:β-OH, wherein $R_4$ is hydrogen or alkyl of one to 4 carbon atoms, inclusive,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;
wherein $R_7$ and $R_8$ are hydrogen, alkyl of one to 12 carbon atoms, inclusive, benzyl, or phenyl, being the same or different;
wherein $R_9$ is hydrogen or hydroxyl; and
wherein X is
(1) trans—$CH$=$CH$—,
(2) cis—$CH$=$CH$—,
(3) —$C$≡$C$—, or
(4) —$CH_2CH_2$—.

I claim:
1. A prostacyclin-type compound of the formula

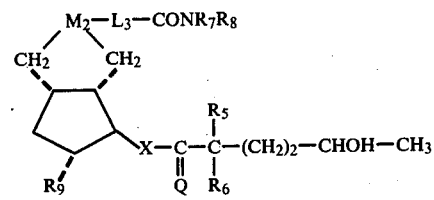

wherein $L_3$ is
(1) —$(CH_2)_n$—, wherein n is one to 5, inclusive,
(2) —$(CH_2)_p$—$CF_2$—, wherein p is 2, 3, or 4, or
(3) —$CH_2$—$CH$=$CH$—;
wherein $M_2$ is

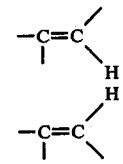 (1)

(2)

wherein Q is oxo, α-H:β-H, α-OH:β-$R_4$, or α-$R_4$:β-OH, wherein $R_4$ is hydrogen or alkyl of one to 4 carbon atoms, inclusive,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;
wherein $R_7$ and $R_8$ are hydrogen, alkyl of one to 12 carbon atoms, inclusive, benzyl, or phenyl, being the same or different;
wherein $R_9$ is hydrogen or hydroxyl; and
wherein X is
(1) trans—$CH$=$CH$—,
(2) cis—$CH$=$CH$—,
(3) —$C$≡$C$—, or
(4) —$CH_2CH_2$—.

* * * * *